United States Patent [19]

Anderson et al.

[11] 4,063,023

[45] Dec. 13, 1977

[54] PROCESS FOR PREPARING 4-(HYDROXYMETHYL)IMIDAZOLE COMPOUNDS

[75] Inventors: Elvin L. Anderson, Moorestown, N.J.; Wilford L. Mendelson, Philadelphia; George R. Wellman, Warminster, both of Pa.

[73] Assignee: SK&F Lab Co., Carolina, P.R.

[21] Appl. No.: 690,476

[22] Filed: May 27, 1976

Related U.S. Application Data

[63] Continuation-in-part of Ser. No. 606,270, Aug. 20, 1975, abandoned.

[51] Int. Cl.$^2$ .......................................... C07D 233/64
[52] U.S. Cl. .................................................... 548/342
[58] Field of Search ........................................ 260/309

[56] References Cited

FOREIGN PATENT DOCUMENTS 2,211,454  10/1972  Germany .......................... 260/309

OTHER PUBLICATIONS

Paquette et al. J. Org. Chem. 1962, vol. 27, pp. 2272–2274.
Tamamushi J. Pharm. Soc. Japan 1933, vol. 53, pp. 664–668.
Remers et al. J. Amer. Chem. Soc. 1967, vol. 89, pp. 5513–5514.
O'Brien et al. J. Chem. Soc. (London) 1960, pp. 4609–4612.

*Primary Examiner*—Natalie Trousof
*Attorney, Agent, or Firm*—Joan S. Keps; Richard D. Foggio; William H. Edgerton

[57] ABSTRACT

An improved process for the preparation of 4-(hydroxymethyl)imidazoles by reducing 4-imidazolecarboxylic acid esters using an alkali metal or calcium in liquid ammonia with an additional proton source provided during the reaction or upon workup.

11 Claims, No Drawings

PROCESS FOR PREPARING 4-(HYDROXYMETHYL)IMIDAZOLE COMPOUNDS

This invention relates to an improved process for the preparation of 4-(hydroxymethyl)imidazole compounds by reducing 4-imidazolecarboxylic acid esters using an alkali metal or calcium in liquid ammonia with an additional proton source provided during the reaction or upon workup.

4-(Hydroxymethyl)imidazole compounds may be prepared by reducing 4-imidazolecarboxylic acid esters using lithium aluminum hydride. This process is expensive, particularly for large scale preparation of 4-(hydroxymethyl)imidazoles.

Tamamushi, *J. Pharm. Soc. Japan* 53: 664–8 (1933), *C.A.* 28:20049 (1934), reported that attempts to reduce 2-methylimidazole-4,5-dicarboxylic acid and ester thereof by various methods were unsuccessful. With the 5-monochloride, reduction with Sn and HCl gave 2-methyl-5-hydroxymethylimidazole-4-carboxylic acid.

It is known to the art that heterocyclic ring systems may be reduced by metals in liquid ammonia via a Birch type reaction. For example, Remers et al., *J. Amer. Chem. Soc.* 89:5513–4 (1967) report that indole and quinoline rings are reduced using lithium and methanol in liquid ammonia. Also, O'Brien et al., *J. Chem. Soc.* 4609–4612 (1960) report that indole and carbazole, but not pyrrole, rings can be reduced by metals in liquid ammonia in the presence of alcohol. According to the process of this invention, the carboxylic acid ester group of a 4-imidazolecarboxylic acid ester is selectively reduced to hydroxymethyl without reducing the imidazole ring by using an alkali metal or calcium in liquid ammonia and an additional proton source.

The process of this invention is advantageous, particularly with the preferred alkali metals, i.e. sodium, potassium and lithium, because the materials used in the reduction of the imidazolecarboxylic acid esters are inexpensive and high yields of the hydroxymethylimidazoles are obtained in a high degree of purity, i.e. at least 90 pure.

The process of this invention may be represented as follows:

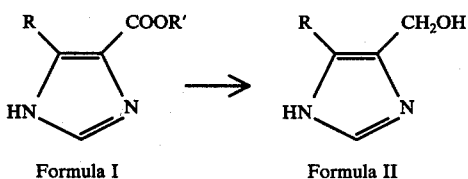

Formula I         Formula II in which R is hydrogen or lower alkyl of 1 to 4 carbon atoms, preferably methyl, and R' is lower alkyl of 1 to 4 carbon atoms, preferably methyl or ethyl.

According to the above process, a lower alkyl ester of a 4-imidazolecarboxylic acid is reduced using an alkali metal or calcium in liquid ammonia with an additional proton source to give a 4-(hydroxymethyl)imidazole. Preferably, an alkali metal is used, most preferably sodium or lithium. Four equivalents of the alkali metal or two equivalents of calcium are required for each equivalent of the ester. Preferably, a slight excess of four equivalents of the alkali metal or a slight excess of two equivalents of calcium is present.

The particular ester of the 4-imidazole-carboxylic acid used is not critical to applicants' process. The lower alkyl esters are advantageous because the alcohols from which they are derived are inexpensive. However, other esters, for example substituted alkyl or aryl esters, such as a benzyl 4-imidazolecarboxylate, may be used alternatively but with little advantage.

A proton source, as required in the process of this invention, is a substance which yields a hydrogen ion. A total of three equivalents of protons per equivalent of ester needs to be provided in order to isolate the free hydroxymethylimidazole compound. They may be provided during the reaction, during the workup or a combination of both. The additional proton sources used in the process of this invention are, most conveniently, commercially available substances.

An alcohol such as, preferably, a lower alkanol containing 1–6, most preferably 2–4, carbon atoms or a cycloalkanol containing, preferably, 5–6 carbon atoms is most conveniently used to provide two of the necessary three equivalents of protons. It may be present in the reaction mixture in any amount up to about two equivalents of alcohol per equivalent of ester. Greater amounts can be used but cause faster loss of the alkali or alkali earth metal due to formation of hydrogen gas. Alternatively, two equivalents or more of the alcohol may be added during the workup. In place of these alcohols, compounds with a pKa in the range of 16–35, preferably 16–18, which are not reduced in the process may be used to supply the initial two protons. For example, the solvent ammonia initially supplies protons when an additional proton source such as an alcohol is not added until the workup phase.

In the workup and after the alcohol addition, four equivalents of protons per equivalent of ester are added from a proton source more acidic than hydroxymethylimidazole such as water, ammonium sulfate, acetic acid or preferably ammonium chloride. Three of these equivalents serve to neutralize the two previously formed equivalents of alkoxide (or other base) plus the one equivalent of alkoxide formed from the imidazole ester during the reduction. The fourth equivalent supplies the last equivalent of protons to the hydroxymethylimidazole anion present at that point. If it is desired to isolate the imidazole alcohol as the acid addition salt, a fifth equivalent of protons must be provided from a suitably strong acid such as hydrogen chloride.

Metals used in this process are, for example, alkali metals, such as sodium, potassium or lithium, or an alkali earth metal, such as calcium. However, from the standpoint of economy for large scale work and ease of handling the process, sodium or lithium is preferable.

The reaction is carried out at or below the boiling point of the ammonia solution or mixture, conveniently at a temperature in the range of about −25° C. to −70° C., preferably about −35° C. to −50° C. Alternatively, the reaction may be carried out at a higher temperature under pressure at which the ammonia is liquid.

It is preferable in the process of this invention to dissolve the metal in liquid ammonia and to add to that solution the imidazolecarboxylic acid ester and an alcohol. Preferably, the ester and the alcohol are added simultaneously either separately or previously mixed; or most conveniently, the alcohol is added, followed immediately by the ester. The last method is particularly convenient for large scale work. When the alcohol is added first followed by the ester, it is preferable to use a less acidic alcohol, such as t-butanol, n-butanol or isopropanol, rather than a lower alkanol such as methanol.

Preferably, the alkaline reaction mixture is worked up by quenching the reaction, for example by adding a alcohol, then adding the more acidic proton source such as ammonium chloride, then evaporating the ammonia. Filtration and concentration give a residue which contains the 4-(hydroxymethyl)imidazole compound of Formula II.

Alternatively, the reaction may be quenched by adding water. Then the 4-(hydroxymethyl)imidazole of Formula II is extracted with an alcohol having 3 to 6 carbon atoms such as n-butanol, n-pentanol or preferably t-butanol. Evaporation of the alcohol from the extracts gives a residue which contains the 4-(hydroxymethyl)-imidazole.

The 4-(hydroxymethyl)imidazole compound is preferably isolated as an acid addition salt, preferably the hydrochloride salt, by treating with an acid during the workup, for example by treating with hydrogen chloride, and crystallizing from a suitable solvent such as isopropanol or preferably from a solvent mixture such as isopropanol/acetone/ethyl ether.

The 4-(hydroxymethyl)imidazoles are useful as intermediates for the production of pharmacologically active compounds, in particular histamine $H_2$-antagonists, for example N-methyl-N'-[2-((5-R-4-imidazolyl)methylthio)-ethyl]thiourea and N-cyano-N'-methyl-N''-[2-((5-R-4-imidazolyl)methylthio)ethyl]guanidine compounds. Histamine $H_2$-antagonists act at histamine $H_2$-receptors which as described by Black et al. (Nature, 1972, 236, 385) may be defined as those histamine receptors which are not blocked by "anthistamines" such as mepyramine but are blocked by burimamide. Blockade of histamine $H_2$-receptors is of utility in inhibiting the biological actions of histamine which are not inhibited by "antihistamines". Histamine $H_2$-antagonists are useful, for example, as inhibitors of gastric acid secretion.

N-Methyl-N'-[2-((5-R-4-imidazolyl)methylthio)-ethyl]thioureas are prepared from the 5-R-4-(hydroxymethyl)-imidazoles of Formula II by reacting the hydroxymethyl compound with crysteamine and then reacting the resulting 5-R-4-[(2-aminoethyl)thiomethyl]imidazole with methyl isothiocyanate.

N-Cyano-N'-methyl-N''-[2-((5-R-4-imidazolyl)-methylthio)ethyl]quanidines are prepared from the 5-R-4-(hydroxymethyl)imidazoles of Formula II by reacting the hydroxymethyl compound with cysteamine and then reacting the resulting 5-R-4-[(2-aminoethyl)thiomethyl]imidazole with N-cyano-N',S-dimethylisothiourea or by reacting the 5-R-4-[(2-aminoethyl)thiomethyl]imidazole compound with dimethyl-N-cyanoimidodithiocarbonate and reacting the resulting N-cyano-N'-[2-((5-R-4-imidazolyl)methylthio)-ethyl]-S-methylisothiourea with methylamine.

These thiourea and cyanoguanidine products prepared from the 4-(hydroxymethyl)imidazoles of Formula II are described in British Pat. No. 1,338,169 and U.S. Pat. Nos. 3,950,333 and 3,950,353.

The 4-(hydroxymethyl)imidazoles are used preferably in the form of acid addition salts such as hydrochloride salts in the above procedures to prepare the thiourea and cyanoguanidine compounds.

The following examples are not limiting but are illustrative of the process of this invention.

In the following examples the yields reported are of the crude isolated products. In each case, except as noted, the product is at least 90 percent pure. The major impurity present from this procedure is ammonium chloride which is usually present to the extent of about 1 to 7% by weight. 5-R-imidazole-4-carboxylic acid is present to the extent of about 1 percent or less providing the preferred procedures are followed but can reach 25–50 percent if the order of addition of ester to alkali metal/calcium-ammonia is reversed (Example 4). In no case were products resulting from reduction of the imidazole ring found. When it is desired to obtain a product of the highest purity, especially when large amounts of 5-R-imidazole-4-carboxylic acid are present, the workup procedurre outlined in Examples 2 and 4 is preferable.

EXAMPLE 1

A 2 liter flask was fitted with an overhead stirrer and a nitrogen inlet and charged with 600 ml. of anhydrous ammonia. A dry-ice acetone cooling bath was provided to aid the collection of ammonia and to cool the reaction. After the ammonia was collected, sodium (33 g., 1.435 m.) was added in portions and dissolved giving a deep blue color. t-Butanol (25 ml., 0.266 m.) was added to this solution. 5-Methyl-4-imidazole-carboxylic acid ethyl ester (50 g., 0.32 m.) was added portionwise. After addition of the ester, the blue solution was stirred for five minutes and methanol (100 ml.) was added dropwise causing the blue color to be discharged after a few ml. had been added. Ammonium chloride (78 g., 1.458 m.) was added in portions. The ammonia was evaporated and isopropanol (700 ml.) was added to the residue and the mixture was refluxed for 30 minutes with vigorous stirring. The mixture was cooled to 40° C. and acidified (pH about 1) with hydrogen chloride gas. Water (10 ml.) was added and the mixture stirred at 50° C. for 30 minutes. The mixture was filtered and the filter cake washed with 200 ml. of warm (40°–50° C.) isopropanol. The solution was concentrated to 100 ml. and diluted with acetone (400 ml.) and ether (100 ml.) The product was collected and dried to give 46.0 g. (96%) of 4-(hydroxymethyl)-5-methylimidazole hydrochloride.

EXAMPLE 2

Alternatively, in the procedure of Example 1, the 4-(hydroxymethyl)-5-methylimidazole may be isolated as the base by the following method:

After the ammonia is removed by evaporation in the procedure of Example 1, isopropanol (700 ml.) is added to the residue and refluxed for 30 minutes with vigorous stirring, the resulting mixture is filtered and the isopropanol removed by evaporating in vacuo to give 4-(hydroxymethyl)-5-methylimidazole as the residue.

EXAMPLE 3

A 12 liter flask was fitted with an overhead stirrer and nitrogen inlet and charged with 6 liters of ammonia. A dry-ice acetone cooling bath was provided to aid in the collection of ammonia and to provide cooling during the reaction. After the ammonia was collected, sodium (335 g., 15.23 m.) was added in portions and dissolved in the ammonia giving a deep blue solution. The addition of sodium required about 15 minutes. 5-Methyl-4-imidazolecarboxylic acid ethyl ester (500 g., 3.25 m.) was added to 400 ml. of dry ethanol giving a wet powder. This wet powder was added portionwise with caution to the sodium-ammonia solution over a period of about 30 minutes. After the addition was completed, one liter of methanol was added carefully. Ammonium chloride (810 g., 15.28 m.) was added very cautiously until the blue color was discharged whereupon the remaining ammonium chloride could be added more rapidly. After the addition of the ammonium chloride, the ammonia was evaporated using a cold water heating bath. As the volume of the mixture decreased, the heating bath was made warmer. When nearly all the ammonia was gone, the mixture was heated with steam under a vacuum to remove the last traces of ammonia. The removal of ammonia requires 7-15 hours. Isopropanol (6 liters) was added to the residue and refluxed for one hour with vigorous stirring. Water (100 ml.) was then added and the stirring continued for 10 minutes. The mixture was then cooled to about 40° C. and acidified with hydrogen chloride gas and filtered. The filter cake was washed with hot isopropanol and the combined filtrate concentrated to about one liter and diluted with 4 liters of acetone and 2 liters of ethyl ether. The product was collected and dried at 60° C. under vacuum to give 4-(hydroxymethyl)-5-methylimidazole hydrochloride, yield 94 percent.

EXAMPLE 4

A suspension of 5-methyl-4-imidazolecarboxylic acid ethyl ester (3.0 g., 0.02 m.) and absolute ethanol (10 ml.) was stirred at dry-ice temperature in a dry 200 ml. flask equipped with a dry-ice condenser as 60-80 ml. of ammonia was added. (Alternatively 10 ml. of t-butanol may be used in place of ethanol).

Small pieces of sodium (from xylene) were added over 15-20 minutes. The solution became clear during the addition, then a blue color persisted for one minute and the solution became clouded. This required 2.2-2.7 g. of sodium. The reaction required 20-30 minutes.

The ammonia was allowed to evaporate and water (50 ml.) and solid sodium chloride were added. The aqueous solution was extracted with several 40 ml. portions of t-butanol. Sodium chloride was added during the course of the extraction.

The alcohol layer was evaporated. The 4-(hydroxymethyl)-5-methylimidazole which was present in the residue was converted to the hydrochloride salt by treating with ether and isopropanol and passing hydrogen chloride gas into the chilled solution. The 4-(hydroxymethyl)-5-methylimidazole hydrochloride (1.6 g., 55%) was isolated by filtration.

EXAMPLE 5

By the procedure of Example 1, using in place of 5-methyl-4-imidazolecarboxylic acid ethyl ester, the ethyl ester of 4-imidazolecarboxylic acid, the product is 4-(hydroxymethyl)imidazole.

Also, reducing 5-ethyl-4-imidazolecarboxylic acid ethyl ester by the procedure of Example 1 gives 5-ethyl-4-(hydroxymethyl)imidazole and reducing 5-isopropyl-4-imidazolecarboxylic acid ethyl ester by the same procedure gives 4-(hydroxymethyl)-5-isopropylimidazole.

EXAMLE 6

A liter flask, fitted with an overhead stirrer and a nitrogen inlet, was charged with 300 ml. of anhydrous ammonia. Potassium (26.0 g., 0.66 m.) was added. t-Butanol (12.5 ml., 0.133 m.) was added, then 5-methyl-4-imidazolecarboxylic acid ethyl ester (25.0 g., 0.16 m.) was added portionwise over 20 minutes. The reaction mixture was stirred for five minutes then quenched with 50 ml. methanol. Ammonium chloride (40.0 g., 0.74 m.) and isopropanol (400 ml.) were added and ammonia removed by distillation. Hydrogen chloride gas was added to about pH 1 and the solids filtered off. The filtrate was concentrated to 60 ml. and acetone (300 ml.) was added. The product was collected by filtration and dried to give 24 g. (98%) of 4-hydroxymethyl)-5-methylimidazole hydrochloride.

EXAMPLE 7

A 2 liter flask, fitted with an overhead stirrer and a nitrogen inlet, was charged with 700 ml. of anhydrous ammonia. Calcium (29.0 g., 0.723 m.) was added carefully in portions. t-Butanol (25 ml., 0.266 m.) was added in one portion and 5-methyl-4-imidazolecarboxylic acid ethyl ester (50 g., 0.32 m.) was added in portions over 30 minutes. The blue solution was stirred for 40 minutes and methanol (120 ml.) added dropwise. Ammonium chloride (80.0 g., 1.48 m.) and isopropanol (800 ml.) were added and the ammonia removed. Hydrogen chloride gas was added (pH about 1) and the solids filtered off. The filtrate was concentrated to 100 ml. and acetone (500 ml.) was added. The product was collected and dried to give 4-hydroxymethyl-5-methylimidazole hydrochloride (23.0 g. of 65% pure material; yield 30%).

EXAMPLE 8

A 2 liter flask was fitted with a nitrogen inlet and an overhead stirrer. With the cooling of a dry ice-acetone bath, approximately 500 ml. of liquid ammonia was collected in the flask. Lithium metal (6.3 g., 0.895 m., about 25 percent excess) was dissolved in liquid ammonia to form a blue solution. With continuous cooling and stirring, 5-methyl-4-imidazolecarboxylic acid ethyl ester (27.58 g., 0.179 mole) was added in very small portions. After the ester was added, the reaction solution remained blue and was stirred for five minutes. The blue solution was quenched by adding dropwise 60 ml. of methanol. Then, oxalic acid powder (41 g., 0.45 mole) was added with caution. Ammonia was evaporated on a hot water bath to obtain a thick slurry which was taken up in 500 ml. of isopropanol. The mixture was heated for ½ hour at 60°-75° C. and cooled before filtering. The filtrate was acidified to pH 1 with hydrogen chloride gas and filtered again. This second filtrate was concentrated to a thick slurry and diluted with acetone. The product was collected and dried to give 20.7 g. (78%) of 4-(hydroxymethyl)-5-methylimidazole hydrochloride.

EXAMPLE 9

A 5 liter flask was fitted with an overhead stirrer and flushed with nitrogen. The vessel was charged with 2.7 liters of anhydrous liquid ammonia without external cooling. After ammonia was collected, sodium (112 g., 4.87 moles) was added in small portions. After the sodium had dissolved, slow stirring was started and 5-methyl-4-imidazolecarboxylic acid ethyl ester (150 g., 0.974 m., formulated as 0.5 g. tablets) was added in 2 g. portions at 25-30 second intervals. The temperature stayed around −28° C. during this addition. After the addition of the ester, the solution remained blue in color. Methanol, 300 ml., was cautiously added dropwise to quency the blue color (if the blue color does not discharge after the methanol addition, the stirring should be continued until it does). Following the methanol addition, ammonium chloride (265 g., 4.97 m. about 2 percent excess of molar sodium) was added portionwise with caution. Following the addition of ammonium chloride, ammonia was evaporated to give a thick slurry. The temperature of the walls of the vessel should not exceed 50° C. Isopropanol (2.1 liters) was added and the mixture was vigorously agitated while warming the mixture to 75° C. The mixture was then acidified with hydrogen chloride gas (to pH about 1) and 30 ml. of water was added. The mixture was stirred for 15 minutes and cooled to 40°-50° C. and filtered. The residue was washed with warm isopropanol (2 × 300 ml.). The filtrate and washing was concentrated to near dryness (thick slurry) and diluted with acetone (about 1.5 liters). The product was collected and dried to give 125.8 g. (87 percent) of 4-(hydroxymethyl)-5-methylimidazole hydrochloride.

EXAMPLE 10

A 5 liter flask was fitted with an overhead stirrer and flushed with nitrogen. The vessel was charged with 2.3 L. of anhydrous liquid ammonia without external cooling. After the ammonia was collected, sodium (97 g., 4.22 m., 25 percent molar excess) was added in portions. When the sodium was dissolved, stirring was started and 5-methyl-4-imidazolecarboxylic acid ethyl ester (130 g., 0.844 m. and formulated as 0.5 g. tablets) was added in 2 g. portions at about 30 sec. intervals. Following the addition of the ester, the blue solution was stirred for five minutes. n-Propanol (260 ml.) was cautiously added dropwise to discharge the blue color (if the blue color does not discharge during the n-propanol addition, the stirring should be continued until it does). Ammonium chloride (232 g., 4.34 m., a 2 percent excess of molar sodium) was added portionwise over 20-30 minutes with caution. The resulting ammonia mixture was evaporated to a thick slurry. The walls of the vessel should not exceed 50° C. n-Propanol (2.0 L.) was then added and the mixture heated to reflux for about 10 minutes to drive off most of the remaining ammonia. The mixture was acidified to pH about 1 with concentrated hydrochloric acid and stirred for 15 minutes while being cooled to about 40° C. The mixture was filtered and the cake washed with 2 × 300 ml. warm (about 40° C.) n-propanol. The filtrate was concentrated under reduced pressure to 300 ml. and the mixture allowed to stand at about 20° C. for 12 hours. The product was collected and dried to give 90.0 g. (72 percent) of 4-(hydroxymethyl)-5-methylimidazole hydrochloride.

EXAMPLE 11

Liquid ammonia, 600 ml., was collected in a 1 liter 3-neck flask equipped with nitrogen inlet and overhead stirrer. Under nitrogen, 18 g. of sodium metal was dissolved in the liquid ammonia and 30.2 g. of 5-methyl-4-imidazolecarboxylic acid ethyl ester was added in small portions over 25 minutes. The reaction mixture remained light blue. Ammonium chloride, 43.4 g., was added in small portions carefully until the blue color disappeared. The rate of addition was increased so that the ammonia was refluxing. At the end of the addition, 400 ml. of isopropanol was added and the mixture was refluxed for 1.5 hours. The suspension was cooled and acidified with hydrogen chloride gas and filtered. The filtrate was concentrated to a slurry and diluted with acetone. The product was dried in a vacuum oven to give 23.2 g. of 4-(hydroxymethyl)-5-methylimidazole hydrochloride.

EXAMPLE 12

A solution of 4-hydroxymethyl-5-methylimidazole hydrochloride (30.0 g.) and cysteamine hydrochloride (23.0 g.) in acetic acid (200 ml.) was heated under reflux for 10 hours. Following cooling to 15°-20° C., the solid which crystallized was collected and washed with isopropyl alcohol to give 4-methyl-5-[(2-aminoethyl)thiomethyl]-imidazole dihydrochloride, m.p. 189°-192° C.

Potassium carbonate (7.75 g.) was added to a solution of 4-methyl-5-[(2-aminoethyl)thiomethyl]imidazole dihydrochloride (14.6 g.) in water (120 ml.). The solution was stored at room temperature for 15 minutes and methyl isothiocyanate (5.15 g.) was added. After heating under reflux for 30 minutes, the solution was slowly cooled to 5° C. The product was collected and recrystallized from water to give N-methyl-N'-[2-((5-methyl-4-imidazolyl)-methylthio)ethyl]thiourea, m.p. 150°-152° C.

EXAMPLE 13

(a) A solution of 4-methyl-5-[(2-aminoethyl)-thiomethyl]imidazole (17.0 g.) and N-cyano-N',S-dimethylisothiourea (11.2 g.) in acetonitrile (500 ml.) was heated under reflux for 24 hours. Following concentration, the residue was chromatographed on a column of silica gel with acetonitrile as eluant and the product obtained was finally recrystallized from acetonitrile-ether to yield N-cyano-N'-methyl-N''-[2-((5-methyl-4-imidazolyl)methylthio)ethyl]-guanidine, m.p. 141°-142° C.

(b) A solution of 4-methyl-5-[(2-aminoethyl)-thiomethyl]imidazole (23.4 g.) in ethanol was added slowly to a solution of dimethyl-N-cyanoimidodithiocarbonate (20.0 g.) in ethanol, with stirring at room temperature. The mixture was set aside overnight at room temperature. Filtration afforded N-cyano-N'-[2-((5-methyl-4-imidazolyl)-methylthio)ethyl]-S-methylisothiourea, m.p. 148°-150° C. The filtrate was concentrated under reduced pressure and the mixture was triturated with cold water and the solid obtained, filtered off and recrystallized twice from isopropyl alcohol/ether to yield further product, m.p. 148°-150° C.

A solution of methylamine in ethanol (33%, 75 ml.) was added to a solution of N-cyano-N'-[2-((5-methyl-4-imidazolyl)methylthio)ethyl]-S-methylisothiourea (10.1 g.) in ethanol (30 ml). The reaction mixture was set aside at room temperature for 2.5 hours. Following concentration under reduced pressure, the residue was recrystallized twice from isopropyl alcohol/petroleum ether, affording N-cyano-N'-methyl-N''-[2-((5-methyl-4-imidazolyl)methylthio)-ethyl]guanidine, m.p. 141°-143° C.

What is claimed is:

1. A process for the preparation of a 4-(hydroxymethyl)imidazole compound of the formula:

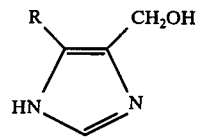

in which R is hydrogen or lower alkyl, which comprises reducing a 4-imidazolecarboxylic acid ester of the formula:

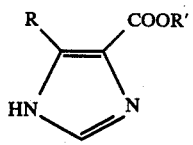

in which R is as defined above and R' is lower alkyl, using an alkali metal or calcium in liquid ammonia with an additional proton source.

2. A process of claim 1 in which the additional proton source is present during the reaction of the ester with the alkali metal or calcium and liquid ammonia.

3. A process of claim 1 in which the 4-(hydroxymethyl)imidazole is isolated as an acid addition salt.

4. A process of claim 1 in which sodium in liquid ammonia is used and the additional proton source is a lower alkanol or cycloalkanol.

5. A process of claim 4 in which 5-methyl-4-imidazolecarboxylic acid lower alkyl ester and a lower alkanol are added to sodium in liquid ammonia.

6. A process of claim 1 in which at least four equivalents of the alkali metal or two equivalents of calcium are present for each equivalent of the 4-imidazolecarboxylic acid ester.

7. A process of claim 1 in which an alkali metal is used.

8. A process of claim 7 in which the alkali metal is sodium.

9. A process of claim 1 in which R is methyl.

10. A process of claim 9 in which R' is methyl or ethyl.

11. A process of claim 10 in which sodium in liquid ammonia is used and the additional proton source is a lower alkanol or cycloalkanol.

* * * * *

UNITED STATES PATENT AND TRADEMARK OFFICE
CERTIFICATE OF CORRECTION

PATENT NO. : 4,063,023
DATED      : December 13, 1977
INVENTOR(S): Elvin L. Anderson, Wilford L. Mendelson and George R. Wellman It is certified that error appears in the above-identified patent and that said Letters Patent are hereby corrected as shown below:

Column 1, line 42, "90" should read -- 90% -- .

Column 3, line 46, "quanidines" should read -- guanidines --.

Signed and Sealed this

Fourth Day of April 1978

[SEAL]

Attest:

RUTH C. MASON
Attesting Officer

LUTRELLE F. PARKER
Acting Commissioner of Patents and Trademarks